United States Patent [19]
Swift et al.

[11] Patent Number: 5,464,742
[45] Date of Patent: Nov. 7, 1995

[54] PROCESS FOR TESTING GENE-DISEASE ASSOCIATIONS

[75] Inventors: Michael R. Swift, 1004 Mt. Carmel Church Rd.; Lawrence L. Kupper; Charles L. Chase, all of Chapel Hill, N.C.

[73] Assignee: Michael R. Swift, Scarsdale, N.Y.

[21] Appl. No.: 137,898

[22] Filed: Oct. 19, 1993

Related U.S. Application Data

[63] Continuation of Ser. No. 562,007, Aug. 2, 1990, abandoned.

[51] Int. Cl.⁶ .............................. C12Q 1/00; C12Q 1/68
[52] U.S. Cl. .................... 435/6; 435/4; 435/91.1; 435/91.2; 536/23.1; 536/24.3; 536/24.31
[58] Field of Search .................... 435/6, 91.1, 4; 536/23.1, 24.3, 24.31

OTHER PUBLICATIONS

Krontiris. et al. Nature. 313:369 (1985).
Swift et al. Am. J. hum. Genet. 39:573–83 (1986).
Berg et al. Nature. 313:369 (1985).
Lander et al. P.N.A.S. 83:7353–57 (1986).
Berg et al. Diabotologia 3:30–34 (1967).
Woolf. B. Ann. Hum. Genet. 19:251–53 (1955).
Schlesselman J. in Case Control Studies. CHAP 6 Sample Size Oxford Univ. Press. N.Y., (1982).
Fleiss J. in. Statistical Methods for Rates and Proportions. Chap 2. Assessing significance in a 4×4 Table John Wiley N.Y. (1984).
Gillis P. Interdi Sci. Reviews. 4(4) 307 (1979).

*Primary Examiner*—W. Gary Jones
*Assistant Examiner*—Paul B. Tran
*Attorney, Agent, or Firm*—Venable, Baetjer, Howard & Civiletti

[57] ABSTRACT

The present invention describes a process to test the association of an allele and a disease, especially a non-Mendelian disease. The process involves a comparison of the proportion of test individuals who have the disease and carry the allele from a set of families in which the allele is present and the proportion of test individuals expected to carry the allele if there is no association between the gene and the disease.

17 Claims, No Drawings

PROCESS FOR TESTING GENE-DISEASE ASSOCIATIONS

The United States Government has rights in this invention pursuant to National Institutes of Health Grants No. CA 14235 and HD 03110, awarded by the U.S. Department of Health and Human Services. This application is a continuation of application Ser. No. 07/562,007, filed Aug. 2, 1990, now abandoned.

BACKGROUND OF THE INVENTION

The present application relates to a process for testing associations of genes and diseases, that is, which specific genes predispose to important common diseases. The invention further relates to a process for selecting a set of families to be used in testing an association between an allele and a disease.

The publications and other materials used herein to illuminate the background of the invention, and in particular, cases to provide additional details respecting its practice, are incorporated herein by reference and for convenience are numerically referenced in the following text and respectively grouped in the appended bibliography.

The determination of the association of a gene with a disease has considerable practical importance, because once a particular gene is known to predispose to a serious disease, there are established procedures for determining how each of these genes acts and for understanding the interaction of existing environmental causes with the gene to produce the serious disease. Just as the discovery of the polio virus and its growth in cell culture led to the highly successful polio vaccines, connecting a specific gene with a specific common disease provides the basis for preventing this disease in genetically susceptible individuals (1–3, for example). The connection of a gene with a disease is also useful for the diagnosis of persons at risk for expressing the disease.

Modern techniques of molecular biology make it possible to identify any human gene for which certain minimal information is known. Given the precision of these laboratory methods, a generally applicable, convincing and systematic process to connect—"associate" is the technically correct term—genes with important common diseases is needed, and has not been available prior to the present invention.

There are limited situations in which it is easy to detect the association of a specific gene with a particular disease. These situations are the inherited diseases that are inherited in what is termed a "Mendelian pattern." An example of such a disease is Huntington's disease. Each person who inherits one copy of a gene for Huntington's disease will develop that disease during his or her lifetime, if he or she lives long enough. From the pattern of inheritance in families with this disorder, it was easy to determine that this disorder was a consequence of a single mutant allele at a particular gene locus. There are diseases, like cystic fibrosis and sickle cell anemia, in which every person who has two alleles for the disease develops it. Other diseases are transmitted through genes located on the X chromosome. While there are several thousand different Mendelian inherited disorders, each of them is individually quite rare and together they do not account for most of the known important predisposition to common diseases. Even though Mendelian disorders contribute little directly to understanding the genetics of common disorders, it is important to begin by describing the prior art with this class, since it is basic to understanding the more complex approaches to the genes for common diseases.

In the first instance, the idea that an autosomal, dominant disorder like Huntington's disease was determined by a single mutant allele at a single genetic locus in each family was inferred from the pattern of inheritance in Huntington's disease families. By now, the idea that Huntington's disease or other Mendelian disorders are each the result of a single mutant allele has been well confirmed through linkage studies and, in certain interesting cases, by identifying the mutant allele itself.

As indicated above, the genes that predispose to serious common diseases such as coronary heart disease, diabetes mellitus, cancer, mental illness, or mental retardation do not produce their clinical effects in such a way that a Mendelian pattern can be observed in families in which one of these genes is transmitted. The basic reason for this fact is that the genes that predispose to these serious common diseases do not produce the common disease in every person who carries the gene. It is known that genes predispose to breast cancer, for example, because breast cancer is more common among first-degree relatives of breast cancer patients than it is in the general population. It is also known that alcoholism or certain forms of mental illness can result from genetic predisposition because the children of alcoholics or mentally ill individuals have a higher risk of developing the same illness, even when they are adopted away from their biological parents early in infancy. Evidence of this sort is available for many common diseases. From this evidence it is known that genes are often important in predisposing to these common diseases, but from these data alone nothing can be learned about the specific genes or mechanisms involved.

The principal approach to identifying a few specific genes that predispose to common diseases has been that of "population association studies." The general concept underlying this approach is that of "allele frequency." At any gene locus in the entire genome, there may be two or more alternative versions of the gene, called alleles. For simplicity, and without any loss of generality, the case in which there are only two alternative alleles at the single locus of interest will be considered. The more common of the two alleles is designated A and the less common allele is designated a. Since the non-sex chromosomes (autosomes) are paired, each person can be homozygous for the common allele, AA, homozygous for the rare alleles, aa, or heterozygous for both alleles, Aa.

In any population of N individuals, there will be a total of 2N copies of this particular gene. Among these 2N alternatives, the proportion of genes that are actually allele a is the allele frequency of a. In the case of only two alternative alleles, the allele frequencies for A and a will sum to 1.00.

It is a basic fact of human population genetics that for any gene locus and pair of alleles, the allele frequency in one population is likely to differ substantially from that in another population. For example, the frequency of allele a might be 0.048 in one precinct in Cincinnati and 0.073 in another. While the population allele frequency can be determined methodically for any population and for any alleles for which there is a totally specific and sensitive test, in practice allele frequencies are only determined in specific situations, such as during the study of a specific indigenous tribe or when blood grouping or HLA typing is done for clinical purposes or as part of a defined population survey.

Population-based tests of gene-disease associations are carried out in the following way. Suppose that allele a is hypothesized to predispose to disease D. To test this hypothesis, the frequency of allele a in a population of patients with disease D is compared to that in a comparison or control population. Evidence for this hypothesized association would consist of finding a significantly higher frequency of the allele in the disease population compared to controls. The allele frequency in the control population is taken to be representative of that in the general population from which the population of individuals with disease D was selected (4).

This population method for detecting important gene-disease associations has been effective in certain limited circumstances, particularly in verifying associations between specific HLA alleles (5) and common diseases, such as ankylosing spondylitis or insulin-dependent diabetes mellitus. It is recognized widely, however, that this approach is severely limited for testing many important gene-disease associations. In fact, because of these limitations, conflicting results have been obtained for a single hypothesized association like that of breast cancer with specific H-ras alleles (6, 7). The most important limitation of population-based tests of gene-disease associations is that it is very difficult to match, for the important stratification variables that influence allele frequency, the population with disease D to a comparison population. As pointed out above, allele frequencies can differ widely between different ethnic groups and even different socio-economic strata because of patterns of migration and mating. This variation is such a dominant source of error that it can give misleading positive or negative results. When the association is extremely strong, such as that of ankylosing spondylitis and HLA B27 (5), this limitation does not apply. Even then, it was important to confirm the association in many different ethnic groups.

The other major limitation on population-based tests of gene-disease associations is that they have relatively poor statistical power. This issue is particularly important because the sample size required to achieve a specified level of statistical power increases dramatically as the allele frequency in the general population falls. Thus, gene-disease associations where the hypothesized disease-predisposing allele has a frequency around one percent, which is the common situation, require extremely large samples, making both the matching of the disease and control group and the replication of the study more difficult. At the present time, many important gene-disease associations are either controversial or have gone entirely untested because of the limitations of the population approach to testing these associations.

It has been proposed that genomic mapping through linkage analysis, a wholly satisfactory procedure for Mendelian conditions, might be applied to localize genes that predispose to common non-Mendelian disorders. Currently available molecular genetic techniques have greatly enhanced the power of genetic and epidemiologic strategies used to identify specific genes that predispose to common chronic diseases. For example, the increasingly detailed genomic map of DNA polymorphisms may make it possible to adapt linkage methods, highly successful for recognized Mendelian syndromes, to map some genes for non-Mendelian chronic disorders (8). However, because of clinical and genetic heterogeneity (9), the practical usefulness of linkage analysis in this setting remains to be determined. At this time, there are no successful practical, general applications of this proposal. It is not clear, in fact, whether the assumptions under which this generalization of linkage analysis is to be carried out are realistic enough for useful results to be obtained. Of all the limitations of generalizing linkage analysis to non-Mendelian diseases, the most important is that these disorders are genetically heterogeneous: genes at many loci can predispose to the same common disorder.

SUMMARY OF THE INVENTION

The present invention is directed to a process for testing individual associations of genes and diseases. More specifically, the process is capable of testing whether an allele is important in predisposing to, i.e., is associated with, this specific disease.

The present process comprises the steps of: (a) selecting a set of families, each family having an index individual who carries a specific allele, and a test individual who has the disease of interest, (b) determining a first proportion of test individuals who carry the allele, (c) determining a second proportion of test individuals expected to carry the allele if there is no association between the specific allele and the specified disease, and (d) statistically comparing the two proportions to determine if said allele and said disease are associated. Because of the unique structure of the sample selected in accordance with the description herein, relatively few individuals need to be tested to produce a statistically significant result and the results are highly unlikely to be affected by intentional or unintentional bias or by differences in baseline allele frequency between populations.

The present invention is further directed to a process for selecting a set of families for use in the process of determining an association of an allele and a disease. This process comprises the steps of (a) selecting a population of individuals; (b) selecting index individuals from that population, the index individuals carrying one or two copies of said allele; (c) determining the presence of said disease within blood relatives of the index individuals; and (d) selecting the set of families, each family having an index individual and a test individual who has the disease and is a blood relative of the index individual. The random population of individuals can be used to select different sets of families for any allele-disease association which is to be tested.

DETAILED DESCRIPTION OF THE INVENTION

The present invention is directed to a process for determining the association between genes and diseases. The process is particularly useful in determining the association between a proposed gene and a particular non-Mendelian disease. The present invention is further directed to a process for selecting a set of families for use in determining the association between an allele and a disease. Each set of families is selected from a random population of individuals, which population can be used for determining the association between any allele and any disease.

In connection with the present invention, the following definitions are provided:

Allele—Any of one or more alternative forms of a given gene, differing in DNA sequence. Allele A is used to exemplify the more common allele, and allele a the less common allele and the one which predisposes to a disease.

Association—The non-random, joint occurrence of two characteristics in a population, such as an allele and a disease, at a frequency that is greater than expected according to the product of their independent frequencies.

Disease—Any abnormal condition that impairs normal physiological function. "Disease" is intended to include such abnormal conditions as cancer, mental illness, diabetes mellitus, hypertension, alcoholism, coronary heart disease, early mortality and the like.

Family—Relatives by pedigree of an index individual.

Index Individual—An individual who carries one or two copies of allele a. The index individual can be identified through a population survey.

Non-Mendelian Disease—A disease in which there is familial aggregation and the inheritance of the expressed disease is not predictable according to Mendelian genetics.

Test Individual—An individual who has the disease of interest and is a blood relative of an index individual.

The process for determining an association between a gene and a disease in its broadest terms is performed by comparing a first proportion of test individuals within a set of families who carry the allele with a second proportion which is the proportion of test individuals expected to carry the allele if there is no association between the allele and the disease. The first proportion is determined from a set of families in which the allele is present. The families; are selected on the basis of an index individual having the allele and a test individual having the disease.

In general terms, the process is performed as follows. Consider an autosomal locus at which there are two alleles, A and a. Further suppose that the rarer allele, a, has been hypothesized to be associated, in the heterozygous state Aa, with disease D. Disease D typically would be a non-Mendelian common disease such as a specific cancer, mental illness, or diabetes mellitus. Such disorders rarely show clear Mendelian patterns in families; for a common disease in which a typical Mendelian pattern is evident, linkage analysis is more suitable than the present method. Select, from the population in which the association of a with D is to be tested, a sample of N' unrelated index individuals who are heterozygous or homozygous for allele a. The index individuals may be homozygous or heterozygous for the allele, since they serve only to identify families in which the allele is segregating; index individuals who may be found through a population survey need not, and typically will not, have disease D.

The next step is to compile pedigrees with reliable clinical information for each of the N' families identified through the index individuals heterozygous or homozygous for a. Using the clinical information, select N blood relatives who have disease D (test individuals) from the N' families, with the following rules. The selected test individual cannot be an index individual. Select only one test individual from the family of each Aa index individual. If the index individual is aa and his parents are not related, one test individual may be selected from the maternal lineage and one from the paternal; this is because allele a is segregating in each lineage and the allele status of each maternal relative is independent of that of each paternal relative. Then, for each of the N selected test individuals, determine his or her genotype at the locus.

The observed proportion of these N test individuals with genotype Aa is then compared to the proportion expected from the familial relationships and from the (assumed to be known) population gene frequency q ($0<q>0.5$) of a. A statistically significant elevation of the observed over the expected proportion indicates a positive association between disease D and Aa status. If the observed proportion is significantly less than the expected proportion, this fact is evidence that allele a protects against disease D. For most chronic diseases, the observed odds ratio estimates reasonably well the relative risk, which is the ratio of the risk of disease for Aa carriers to the risk for AA non-carriers.

DESCRIPTION OF THE PREFERRED EMBODIMENTS

In its broadest terms, the process for determining the association of an allele and a disease comprises the steps of (a) selecting a set of families, each family having an index individual who carries a specific allele and a test individual who has the disease of interest, (b) determining empirically a first proportion of test individuals who carry the allele, (c) determining a second proportion of test individuals expected to carry the allele if there is no association between the specific allele and the specified disease, and (d) statistically comparing the two proportions to determine if said allele and said disease are associated. The process for selecting a set of families comprises the steps of (a) selecting a random population of individuals; (b) selecting index individuals from that population, the index individuals carrying one or two copies of said allele; (c) determining the presence of said disease within blood relatives of the index individuals; and (d) selecting the set of families, each family having an index individual and a test individual who has the disease and is a blood relative of the index individual.

The process according to the present invention provides for a broad choice of each of the following items:

(1) the hypothesis to he tested;
(2) the genetic locus to be studied;
(3) the specific allele or set of alleles hypothesized to predispose to disease D;
(4) the disease n to he investigated for its association with the putative disease-predisposing allele(s); and
(5) the population in which the gene-disease association is to he tested.

Hypotheses

There is no restriction on the hypotheses to be tested, except that the selection of the hypothesized disease-predisposing allele(s) and of disease D follow the broad principles described below.

The process according to the present invention can be used to test existing hypotheses that need to be confirmed. For example, a gene-disease association for which data from population studies are conflicting or unconvincing can be tested reliably using the process of the invention. Similarly, a gene-disease association hypothesized on the basis of clinical observations can be tested rigorously in one step with this process. Another way in which hypotheses may be generated from existing information and tested with the present process is to hypothesize a gene-disease association on the basis of the known biochemistry and physiology of the gene. For example, the conjecture that a variant allele of a gene that controls the action of a neurotransmitter in the brain might be responsible for a certain type of mental illness can be tested rigorously with the method described herein.

Gene Locus

Any of the estimated 50–100,000 human gene loci can be evaluated provided there is a specific and sensitive test for the different alleles at that locus. The test to distinguish alleles can be based on any methodology that is wholly sensitive and specific. Examples of such tests include, but are not limited to, the protein electrophoresis or immunochemical tests for the PiZ allele at the alpha$_1$ antitrypsin locus or the DNA tests for the delta$_{508}$ allele at the cystic fibrosis locus or the translocations within the neurofibromatosis gene. The appropriate test to utilize for a given allele is within the skill of the art to select.

Selection of Population

The population in which the hypothesis is to be tested can be selected arbitrarily for experimental convenience or according to defined requirements. The population is defined by the selection from it of index individuals, as described below. For example, it might be convenient to select the index individuals from paid college student volunteers. On the other hand, it might be necessary to select the index individuals from a random sample of the United States population. Either is possible, and useful in providing a valid determination of the association between a gene and a disease.

Selection of Hypothesized Disease-Predisposing Allele

There must be a definite test for the allele. This test will typically be a DNA-based test, although there are alleles for which other laboratory methods will be simpler and more convenient. As discussed above, such tests are known or can readily be determined by skilled artisans.

Definition Of Disease D

Flexibility in the definition of disease D means that this definition can be selected to be an accurate representation of the precise hypothesis. It can be as general as the concept of "early mortality." It could be as precise as "intraductile breast cancer with onset between ages 45 and 49." For example, if a specific allele at a given genetic locus is hypothesized to predispose to mental illness, but the precise form of the mental illness is not known, disease D could be "hospitalization in a psychiatric hospital or ward." Then, if the present process confirms the association of the allele and disease D defined in this manner, the nature of the gene-associated psychiatric disease could be narrowed by examining the characteristics of the illness in those who were found to carry the allele in the initial test of the hypothesis. From these data a new, more precise definition of disease D could be formulated and a new test of the association carried out, based on this new definition. Two or more recursive steps of this type would yield a quite precise characterization of the psychiatric illness associated with the specific allele.

Process of Determining an Association Between an Allele and a Disease

The process according to the present invention entails four steps. Briefly, these steps are: (a) selecting a set of families of persons having a specific segregating allele, (b) determining a first proportion of said persons having both the specified disease and the allele, (c) determining a second proportion, said second proportion being the proportion of persons expected to carry the allele if there is no association between the specific allele and the specified disease, and (d) statistically comparing the two proportions to determine if said allele and said disease are associated. These steps are now described in further detail.

For a specific hypothesis with a selected genetic locus, hypothesized disease-predisposing allele a, and a defined disease D, the first step is to select a set of families in which allele a is known to be segregating. Each family is identified through a single individual, called an index individual, for whom either totally reliable clinical data or a specific laboratory test demonstrate that this individual carries one or two copies of allele a. Since mutation rates in humans are so low, the fact that the index individual carries allele a is sufficient evidence that this allele is transmitted in said individual's family.

The way in which an index individual is found depends on the character of allele a. In many cases, allele a can only be detected though a specific assay done on a blood sample. In these cases, index individuals are found through collecting blood samples from a volunteer population and analyzing them for the presence of allele a.

When the entire set of index individuals has been ascertained as described above, individuals other than the index individual, with disease D, are identified in each family of an index individual by reviewing comprehensive pedigrees with medical information, typically compiled by questionnaire or interview of each index individual. For each relative who may have disease D according to the anecdotal pedigree, medical records are obtained to determine if that person does have the disease.

After these records have been characterized, a set of families is obtained in which allele a is segregating and in which at least one relative of the index individual has disease D. In these families, specific relatives with disease D (termed test individuals) are selected according to the following rules. If the index individual in the family is heterozygous for allele a, then only one test individual is selected from that family. If more than one relative has disease D, the selection of a single test individual may be arbitrary or it may follow the guidelines for maximizing statistical power. If the index individual in a particular family is homozygous for allele a, one test individual may be selected from both the maternal and paternal sides of the family.

Another approach is based on the fact that some disease-predisposing genes cause a distinctive autosomal recessive syndrome in homozygotes. When this is the case, families in which the allele of interest is segregating may be found by collecting a series of patients with the distinctive autosomal recessive syndrome. Since with this method, the index individual in each family must be homozygous for allele a, then one test individual may be selected from both the maternal and paternal sides of the family.

A third method for finding families with both disease D and allele a may be the most efficient in certain settings. Given an existing collection of DNA or blood samples from unrelated persons with definite disease D (potential test individuals), a single close relative could be tested for allele a. When this relative tests positive for allele a, the original test individual in the family would be a member of the set of test individuals to be evaluated at the next step.

With any of these three approaches, a set of test individuals is obtained who have disease D from different families in which allele a is definitely segregating. The next two steps—one empirical, the second analytic—provide two numbers which are compared using the score statistic to evaluate the significance of the difference.

Using the reliable assay for allele a, the selected test individuals are tested to identify who has allele a. The proportion (observed) of the selected test individuals who actually carry the allele is then determined. Using standard statistical methods of population and quantitative genetics, the proportion (expected) of test individuals with allele a in this sample that would be expected from genetic principles if there were no association between disease D and allele a is determined. If the difference between these two proportions—the observed and the expected—is statistically significant, i.e., the observed proportion is significantly elevated over the expected proportion, then the allele a is positively associated with disease D. If the observed proportion is significantly less than the expected proportion, then allele a protects against disease D. The relative risk of a heterozygote having the disease, which estimates the strength of the association, is determined by the odds ratio.

STATISTICAL CONSIDERATIONS

Null Probabilities of Being Heterozygous for Allele a for Blood Relatives of a Known Aa Heterozygote or aa Homozygote Three scenarios are considered: (I) the index individual is an Aa heterozygote; (IIA) the index individual is is an aa homozygote who is clinically normal; and (IIB) the index individual is an aa homozygote, and aa homozygotes are all clinically abnormal (or aa is "genetically lethal"). Scenario IIB applies when the index individuals all have a specific autosomal recessive syndrome, such as ataxia-telangiectasia. The indviduals with the syndrome need not have disease D, although it is likely that they themselves do have a high risk of developing it. For the first two scenarios, standard methods (10, 11) provide exact expressions (functions of q, the frequency of allele a; Table I, Parts A and B) for the conditional probabilities that blood relatives of the index individual are Aa, assuming random mating, and that no mating pair has genes identical by descent. These probabilities are the proportions of the test individuals that are expected to be heterozygous for allele a under the null hypothesis of no association between the heterozygous state Aa and disease D. Standard conditional probability arguments are used to derive the null probabilities under Scenario IIB (Table I, Part C), in which the rare aa relative will be readily recognized and excluded from the analysis because he/she will have the distinctive phenotype of the autosomal recessive syndrome of the index individuals.

TABLE I

A. Conditional probability, Θ, of a relative of a known heterozygote (Aa) being heterozygous (Aa) for selected values of the allele frequency (q) in the population under study.[a] (Scenario I)

| q | Sibling[b] | Second-Degree Relative[c] | First Cousin[d] |
|---|---|---|---|
| .001 | .5005 | .2510 | .1265 |
| .005 | .5025 | .2550 | .1325 |
| .010 | .5049 | .2599 | .1399 |
| .030 | .5145 | .2791 | .1687 |
| .050 | .5237 | .2975 | .1963 |
| .100 | .5450 | .3400 | .2600 |
| .200 | .5800 | .4100 | .3650 |

[a]The conditional probability of a parent or child of a known heterozygote (Aa) being heterozygous (Aa) is 0.5 independent of the allele frequency.
[b]$(1 + q - q^2)/2$
[c]$(1 + 4q - 4q^2)/4$ (grandparent, aunt, uncle, niece or nephew)
[d]$(1 + 12q - 12q^2)/8$ B. Conditional probability, Θ, of a relative of a clinically normal homozygote (aa) being heterozygous (Aa) for selected values of the allele frequency (q) in the population under study. (Scenario IIA)

| q | Child or Parent[a] | Sibling[b] | Second-Degree Relative[c] | First Cousin[d] |
|---|---|---|---|---|
| .001 | .9990 | .5000 | .5005 | .2512 |
| .005 | .9950 | .5000 | .5025 | .2562 |
| .010 | .9900 | .4999 | .5049 | .2623 |
| .030 | .9700 | .4996 | .5141 | .2862 |
| .050 | .9500 | .4988 | .5225 | .3088 |
| .100 | .9000 | .4950 | .5400 | .3600 |
| .200 | .8000 | .4800 | .5600 | .4400 |

[a]$(1 - q)$
[b]$(1 - q^2)/2$
[c]$(1 + q - 2q^2)/2$
[d]$(1 + 5q - 6q^2)/4$

TABLE I-continued

C. Conditional probability, Θ, of a relative of a clinically abnormal homozygote (aa) being heterozygous (Aa), conditional on such relatives and their mates not being aa, for selected values of the allele frequency (q) in the population under study.[a] (Scenario IIB)

| q | Grand-Parent[b] | Aunt or Uncle[c] | Niece or Nephew[d] | First Cousin[e] |
|---|---|---|---|---|
| .001 | .5005 | .5001 | .3338 | .2506 |
| .005 | .5025 | .5006 | .3355 | .2531 |
| .010 | .5050 | .5013 | .3377 | .2562 |
| .030 | .5150 | .5038 | .3464 | .2683 |
| .050 | .5250 | .5063 | .3548 | .2800 |
| .100 | .5500 | .5128 | .3750 | .3079 |
| .200 | .6000 | .5263 | .4118 | .3578 |

[a]Under Scenario IIB, the conditional probabilities of a parent and a sibling of the index individual being heterozygous (Aa) are 1.0 and 2/3, respectively, independent of the allele frequency.
[b]$(1 + q)/2$
[c]$2/(4 - q)$
[d]$(1 + 2q)/(3 + 2q)$
[e]$(1 + 3q - q^2)/(4 + 2q - q^2)$ Tests of significance and related assessments of statistical power depend on these null probabilities. Table I shows that inaccuracy in the measurement of q is unlikely to affect statistical inferences in most practical circumstances. First, even varying q two-fold to five-fold has little effect on the null probabilities for close relatives of the index individual (e.g., parents, children, and siblings in scenario I). Second, for almost all degrees of relationship, there is little variation in the null probabilities for all values of q<0.03. The population frequencies of hypothesized disease-predisposing alleles typically fall in this range. The accuracy of the measurement of q is of much greater importance for allele frequencies higher than 0.03 and when relatives as distant as first cousins are included in the sample. For alleles whose frequency is 0.10 or higher and somewhat uncertain, alternatives to the present method should be used to test hypothesized associations. If the source population is composed of two or more sub-populations with widely discrepant values of q, it is appropriate to analyze such sub-populations separately.

Statistical Inference and Sample Size Considerations

As stated above, to avoid certain dependency-related complications, the present process dictates choosing either (1) exactly one test individual for each identified Aa heterozygote, or (2) one diseased maternal test individual and one diseased paternal test individual of each aa homozygote.
Probability Model
For the i-th test individual (i=1, 2, . . . , N), define the dichotomous random variable $R_i$ to be $$R_i = \begin{cases} 1 & \text{if the } i\text{-th test individual is heterozygous } (Aa), \\ 0 & \text{if not.} \end{cases}$$

Note that $R_i=0$ if the i-th test individual is either AA or aa under scenarios I and IIA. The aa genotype in relatives is excluded under scenario IIB, since these relatives will have the distinctive phenotype of the autosomal recessive syndrome in the index individuals.

Now, let $\Theta_i = pr(R_i=1|D)$. And, under $H_o$: "no association between being a heterozygote and disease risk", let $\Theta_{oi}$ denote the null value of $\Theta_i$. Given the familial relationship of the i-th selected test individual and the known value of q, the specific numerical value of $\Theta_{oi}$ (the null probability that this i-th blood relative is heterozygous Aa) is determined using the methods of the previous section. Under $H_A$: "positive association between being a heterozygote and disease risk", $\Theta_i$ is greater than $\Theta_{oi}$ for i=1, 2, ..., N. The methods apply also to testing for a protective, as opposed to a detrimental, effect of heterozygosity. When an allele protects against disease D, $\Theta_i$ is less than $\Theta_{oi}$, i=1, 2, ..., N.

The effect measure of interest will be the odds ratio (26)

$$\phi = \frac{\Theta_i/(1-\Theta_i)}{\Theta_{oi}/(1-\Theta_{oi})}, \quad 0 < \phi < +\infty.$$

This odds ratio will not depend on i unless other risk factors for disease D are non-randomly distributed with respect to allele a. Note that $$\Theta_i = \frac{\phi \Theta_{oi}}{1 + \Theta_{oi}(\phi - 1)}, \text{ so that}$$

$$\overline{\Theta} = \frac{\phi}{N} \sum_{i=1}^{N} \frac{\Theta_{oi}}{1 + \Theta_{oi}(\phi - 1)}.$$

In terms of $\phi$, the null hypothesis of interest is $H_o$: $\phi=1$, and the alternative hypothesis is either $H_A$: $\phi>1$ for a hypothesized detrimental effect of heterozygosity, or $H_A$: $\phi<1$ for a protective effect of heterozygosity.

Maximum likelihood methods

Since the $\{R_i\}$ are mutually independent 0–1 random variables, the likelihood function L for these data is $$L = \prod_{i=1}^{N} \left\{ \left[ \frac{\phi \Theta_{oi}}{1 + \Theta_{oi}(\phi - 1)} \right]^{R_i} \left[ \frac{(1 - \Theta_{oi})}{1 + \Theta_{oi}(\phi - 1)} \right]^{1-R_i} \right\}.$$

Equating $dL/d\phi$ to zero gives $\hat{\phi}$, the maximum likelihood estimator of $\phi$, as the solution to the likelihood equation $$\sum_{i=1}^{N} R_i = \sum_{i=1}^{N} \left[ \frac{\phi \Theta_{oi}}{1 + \Theta_{oi}(\phi - 1)} \right]. \quad \text{(Eq. 1)}$$

In general, equation (1) must be solved iteratively. A good starting value for this iteration process is $$\frac{\overline{R}/(1-\overline{R})}{\overline{\Theta}_o/(1-\overline{\Theta}_o)}, \text{ where } \overline{R} = N^{-1} \sum_{i=1}^{N} R_i$$

is the observed proportion of test individuals who are heterozygous and where $$\overline{\Theta}_o = N^{-1} \sum_{i=1}^{N} \Theta_{oi}$$

is the expected value of $\overline{R}$ under $H_o$.

Since $$\frac{\ln\hat{\phi} - \ln\phi}{[\widehat{Var}(\ln\hat{\phi})]^{1/2}} \sim N(0,1)$$

for moderate to large N (12), it can be shown that an approximate $100(1-\alpha)\%$ confidence interval for $\phi$ is $$\hat{\phi} \exp\{\pm Z_{1-\alpha/2}[\widehat{Var}(\ln\hat{\phi})]^{1/2}\}. \quad \text{(Eq. 2)}$$

$$\widehat{Var}(\ln\hat{\phi}) = \left[ \hat{\phi} \sum_{i=1}^{N} \frac{\Theta_{oi}(1 - \Theta_{oi})}{[1 + \Theta_{oi}(\hat{\phi} - 1)]^2} \right]^{-1}. \quad \text{(Eq. 3)}$$

Power and sample size considerations

To test $H_o$ versus $H_A$, the use of the score test statistic $(\overline{R} - \overline{\Theta}_o)/[V(\overline{R}|H_o)]^{1/2}$, where $$V(\overline{R}|H_o) = N^{-2} \sum_{i=1}^{N} \Theta_{oi}(1 - \Theta_{oi})$$

is preferred (27). Under $H_o$, this test statistic will have an approximate standard normal distribution for moderate to large N. Hence, the approximate power (28) of a size $\alpha$ test of $H_o$: $\phi=1$ versus $H_A$: $\phi>1$ equals $$pr\left[ \frac{(\overline{R} - \overline{\Theta}_o)}{\left[ N^{-2} \sum_{i=1}^{N} \Theta_{oi}(1 - \Theta_{oi}) \right]^{1/2}} > Z_{1-\alpha} \mid \phi > 1 \right],$$

where $pr(Z>Z_{1-\alpha})=\alpha$ when $Z \sim N(0,1)$. Thus, to achieve a power of at least $(1-\beta)$, standard statistical arguments dictate that N should be the smallest positive integer satisfying the inequality $N \geq$ $$\frac{Z_{1-\alpha}\left[ \sum_{i=1}^{N} \Theta_{oi}(1-\Theta_{oi}) \right]^{1/2} + Z_{1-\beta}\left[ \sum_{i=1}^{N} \Theta_i(1-\Theta_i) \right]^{1/2}}{(\overline{\Theta} - \overline{\Theta}_o)}$$

Since $$N\overline{\Theta}_o(1 - \overline{\Theta}_o) \geq \sum_{i=1}^{N} \Theta_{oi}(1 - \Theta_{oi}) \text{ and}$$

$$N\overline{\Theta}(1 - \overline{\Theta}) \geq \sum_{i=1}^{N} \Theta_i(1 - \Theta_i),$$

an upper bound for N is that positive integer, say N, satisfying the inequality $$N^* \geq \frac{\{Z_{1-\alpha}[\overline{\Theta}_o(1-\overline{\Theta}_o)]^{1/2} + Z_{1-\beta}[\overline{\Theta}(1-\overline{\Theta})]^{1/2}\}^2}{(\overline{\Theta} - \overline{\Theta}_o)^2}.$$

Let us assume that $$\overline{\Theta} \approx \frac{\phi \overline{\Theta}_o}{1 + \overline{\Theta}_o(\phi - 1)}.$$

This assumption is exactly true when the test individuals are all of the same type. In most practical situations, the absolute difference between the exact and approximate values of $\Theta$ should be less than 0.05.

Combining the above approximation with the previous inequality involving $N^*$ gives the inequality $$N^* \geq \frac{\{Z_{1-\alpha}[1 + \overline{\Theta}_o(\phi - 1)] + Z_{1-\beta}\phi^{1/2}\}^2}{\overline{\Theta}_o(1 - \overline{\Theta}_o)(\phi - 1)^2}. \quad \text{(Eq. 4)}$$

The motivation behind the development leading to equation 4 is now apparent. To use equation 4 to help design a study according to the present invention (i.e., to obtain an approximate idea of the needed number $N^*$ of test individuals), it is only necessary to specify values for the following quantities: $\alpha$, the size of the rejection region for a one-sided test of $H_o: \phi=1$ versus either $H_A: \phi>1$ or $H_A: \phi<1$; $(1-\beta)$, the desired power of the test; $\phi$, the anticipated value of the population odds ratio (a value greater than 1 for a detrimental effect of being a heterozygote, and a value less than 1 for a protective effect); and, $\overline{\Theta}_o$, the mean of the N $\Theta_{oi}$ values based on the types of test individuals likely to be chosen and on the value of q. Table II contains values of $N^*$ based on equation 4 for some combinations of values of $\alpha$, $(1-\beta)$, $\phi$, and $\overline{\Theta}_o$. When the anticipated true value of $\phi$ is greater than 2.0, note that $N^*$ does not vary much with changes in $\overline{\Theta}_o$. Table II also demonstrates that a relatively small increase in sample size results in a significant increase in power.

TABLE II

A. Sample sizes ($N^*$) from equation 4 required to test $H_o: \phi = 1$ versus $H_A: \phi > 1$ with power at least $(1 - \beta)$ for $\alpha = .01$, for selected values of the odds ratio ($\phi$), and of the expected proportion of the heterozygotes under the null hypothesis ($\overline{\Theta}_o$).

| | $1 - \beta = 0.75$ | | | $1 - \beta = 0.80$ | | | $1 - \beta = 0.85$ | | |
|---|---|---|---|---|---|---|---|---|---|
| | A[1] | B[2] | C[3] | A[1] | B[2] | C[3] | A[1] | B[2] | C[3] |
| 1.5 | 348 | 234 | 233 | 392 | 262 | 259 | 445 | 296 | 290 |
| 2.0 | 104 | 76 | 84 | 118 | 85 | 93 | 135 | 96 | 104 |
| 2.5 | 54 | 42 | 51 | 61 | 47 | 56 | 70 | 54 | 63 |
| 3.0 | 35 | 29 | 37 | 40 | 32 | 41 | 46 | 37 | 45 |
| 3.5 | 25 | 22 | 30 | 29 | 25 | 33 | 34 | 28 | 36 |
| 4.0 | 20 | 18 | 26 | 23 | 20 | 28 | 26 | 23 | 31 |
| 4.5 | 16 | 15 | 23 | 19 | 17 | 25 | 22 | 19 | 27 |
| 5.0 | 14 | 14 | 21 | 16 | 15 | 23 | 18 | 17 | 25 |

[1] $\overline{\Theta}_o = 0.15$
[2] $\overline{\Theta}_o = 0.30$
[3] $\overline{\Theta}_o = 0.55$ B. Sample sizes ($N^*$) from equation 4 required to test $H_o: \phi = 1$ versus $H_A: \phi < 1$ with power at least $(1 - \beta)$ for $\alpha = .01$, for selected values of the odds ratio ($\phi$), and of the expected proportion of the heterozygotes under the null hypothesis ($\overline{\Theta}_o$).

| .25 | 81 | 39 | 21 | 87 | 42 | 23 | 93 | 46 | 26 |
|---|---|---|---|---|---|---|---|---|---|
| .50 | 217 | 115 | 76 | 237 | 126 | 85 | 261 | 140 | 95 |

[1] $\overline{\Theta}_o = 0.15$
[2] $\overline{\Theta}_o = 0.30$
[3] $\overline{\Theta}_o = 0.55$ Also, from equation 4 and from the entries in Table II, it is clear that, for a given value of $\phi$, the required sample size increases as $\overline{\Theta}_o$ gets closer to zero. Hence, the proposed "enrichment process" of making the null probabilities of heterozygosity larger than $2q(1-q)$ via the use of relatives of index individuals known to carry allele a leads to a statistically powerful design.

Finally, for fixed values of $\alpha$, $\beta$, and $\phi$, the choice of $\overline{\Theta}_o$, say $\overline{\Theta}_o^*$, which minimizes the right-hand-side of inequality 4 is $$\overline{\Theta}_o^* = \left[ 1 + \frac{(Z_{1-\alpha}\phi + Z_{1-\beta}\phi^{1/2})}{(Z_{1-\alpha} + Z_{1-\beta}\phi^{1/2})} \right]^{-1}.$$

Since this optimal $\overline{\Theta}_o^*$ varies inversely with $\phi$, the power of the present method to detect the effects of genes that protect against a disease is much greater when the test individuals are close, rather than more distant, relatives of the index individuals (Table II, Part B).

ILLUSTRATIVE EXAMPLE

The following hypothetical example shows how the present invention is used to assess whether females heterozygous for the ataxia-telangiectasia (A-T) gene are at elevated risk for developing breast cancer (13). The A-T gene has been mapped to chromosome 11q22-23 (14), so that A-T heterozygotes can be identified in A-T families by closely linked markers or allele-specific probes.

Suppose that $N'=60$ families of A-T homozygotes are surveyed and that 10 grandmothers and 10 aunts with breast cancer (test individuals) are found. The best currently available estimates of the A-T allele frequency are that it falls between 0.0012 and 0.02 (33). Assuming that $q=0.01$, then the null probabilities of heterozygosity for the grandmothers and aunts are, respectively, $(1+q)/2 = 0.5050$ and $2/(4-q) = 0.5013$ (see Table I, Part C). Hence, $$\overline{\Theta}_o = 20^{-1} \sum_{i=1}^{20} \Theta_{oi} = [10(.5050) + 10(.5013)]/20 = .5031$$

and $$V(\overline{R}|H_o) = 20^{-2} \sum_{i=1}^{20} \Theta_{oi}(1 - \Theta_{oi}) = [10(.5050)(.4950) +$$

$$10(.5013)(.4987)]/400 = .0125$$

If $$\sum_{i=1}^{20} R_i = 16$$

of these $N=20$ female breast cancer cases are found to be heterozygous for the A-T gene, then $\overline{R}=16/20 =0.80$. The score statistic value is $(0.80-0.5031)/(0.0125)^{1/2}=2.66$ ($p\approx0.0004$), indicating a highly significant association for these data.

From equation 1, the maximum likelihood estimate $\hat{\phi}$ of the population odds ratio $\phi$ is $\hat{\phi}=3.95$. And, from equations 2 and 3, an approximate 95% confidence interval for $\phi$ is (1.32, 11.82). From this odds ratio, it is estimated that an A-T heterozygote has four times the risk of developing breast cancer compared to someone who does not carry this allele.

Comparison with an Alternative Strategy

Sample size requirements for the present invention based on equation 4 have been compared to those for a study design that is believed to be the closest to the present invention. The obvious alternative design is the 1-to-M matched case-control design, where each case is a family member with the disease of interest, each set of M controls consists of M randomly chosen non-test individuals for each case, the dichotomous exposure outcome variable pertains to being heterozygous or not, and the basic matching variable pertains to family membership.

The differences between sample size requirements based on equation 4 and those based on the standard conditional analysis of 1-to-M matched data (see 15, Table 7.9) are so large that adjustments for possible intra-familial correlation effects (16) would not alter the obvious conclusion. In particular, for $\alpha=0.05$, $(1-\beta)=0.80$, and $\bar{\Theta}=0.30$, Table III illustrates that the N* values are much less than the corresponding N$^+$ values of Breslow and Day (15), where the required number of 1-to-M matched case-control sets equals $N_+/(M+1)$.

TABLE III

Sample size requirements for $\alpha = 0.05$, $(1 - \beta) = 0.80$ and $\bar{\Theta}_o = 0.30$ using the present method (N*) compared to 1-to-M matched data method (N$^+$).[a]

| Odds Ratio | N* Values | N$^+$ Values | | |
|---|---|---|---|---|
| | | M = 1 | M = 2 | M = 4 |
| 1.50 | 163 | 710 | 792 | 1,095 |
| 2.00 | 53 | 244 | 270 | 370 |
| 2.50 | 30 | 142 | 156 | 215 |
| 3.00 | 20 | 100 | 111 | 150 |
| 3.50 | 16 | 78 | 87 | 115 |
| 4.00 | 13 | 64 | 72 | 95 |
| 4.50 | 11 | 56 | 60 | 85 |
| 5.00 | 10 | 50 | 54 | 75 |

[a]See reference 15, Table 7.9.

One obvious reason for the large discrepancies between the N* and N$^+$ values is due to the statistical fact that the value of q (or, equivalently, $\bar{\Theta}_o$) is assumed to be known when determining N*, while N$^+$ reflects the necessity to estimate background rates.

Other Characteristics of the Present Method

Effects of Sample Stratification and of Other Risk Factors

Undetected stratification is likely to affect population-based tests of associations but not the method of the present invention, even though there is no explicit control group matched, for potential confounders, to the diseased relatives. In the present method, test individuals are selected from the extended families of the index individuals. Within either the maternal or paternal family of each index individual, heterozygotes and non-heterozygotes for allele a are first-, second-, and third-degree relatives who share both a high proportion of their other genes and the familial environment, including ethnic origins and socio-economic status (SES). Alleles at other loci and environmental risk factors (unless causally related to the allele) are expected to be distributed randomly among allele a heterozygotes and non-heterozygotes in each family. In general, selection bias is unlikely because test individuals are chosen without any knowledge of their status at the locus of interest.

Using the example of an association between allele a and breast cancer, consider how risk factors such as SES or parity might influence the assessment of this association. Any risk factor is either distributed randomly with respect to allele a in each family, or it is not. If the risk factor is randomly distributed with respect to allele a, association cannot be influenced by the factor. Suppose, on the other hand, that allele a predisposes to low parity, which in turn predisposes to breast cancer. Then an association between allele a and breast cancer will be found. This is a true association, mediated through the effect of allele a on parity. Establishing a gene-disease association does not explicate its biological mechanism, which must be determined from further studies or from information already available about how the gene acts.

A true association between allele a and breast cancer might be missed only if the allele had two opposing effects. The allele might predispose to the cancer on the basis of some cellular mechanism related to tumor growth, and also predispose to high parity, which reduces the chance that a breast cancer will develop. This unlikely situation would be detected only by comparing the parity of allele a heterozygotes to non-heterozygotes in the families.

The strategy of the present invention can be adapted to test hypotheses of the form "allele a is associated with significant excess mortality by (or enhanced survival to) age A" by selecting at random from the family of each index individual one living person slightly older than age A. If allele a leads to excess mortality, the observed proportion of allele a heterozygotes in this group will be less than expected. Hypotheses about the effect of specific alleles on mortality are, of course, of substantial biological interest. If such an effect is suspected, it is important to detect and evaluate it before evaluating hypotheses about the allele and a specific disease, since tests of the latter association could be misleading if the allele differentially affects mortality.

When there is incomplete cooperation from the selected set of test individuals, the observed odds ratio will be unbiased unless allele a influences the chance that a relative will be available to, or cooperate in, the study. Thus, if allele a is associated with a severe personality disorder, the sample of N individuals with disease D might not accurately represent the proportion of allele a heterozygotes in the population of interest. This potential source of bias must always be taken into account in testing hypotheses about alleles that predispose to mental disorders.

While the selection of index individuals can be arbitrary, it is important since this set of individuals defines the source population. For example, if the index individuals are selected from a population in which there are two sub-populations in one of which the allele a is not present, then the assessment of heterozygote risk will apply only to the sub-population in which it is prevalent. As always, any association found in one population should be generalized with great care to other populations.

Another way in which the test of an association depends on the source population is illustrated by the test of the hypothesized h-ras breast cancer association in a set of families in which three or more first- or second-degree relatives have had breast cancer (17). In these families, the breast cancers may result from a gene or environmental factor whose effect is so pronounced that effects of alleles at the h-ras locus are not detectable. On the other hand, if the N' families are selected from a general population and the observed proportion of heterozygotes is compared to that expected in this sample, then a positive association of the h-ras allele with breast cancer might be detected.

Specificity of the Hypothesis

The particular group of test individuals will specify the disease phenotype whose association with allele a is being tested. For example, if disease D is breast cancer and all relatives with breast cancer in the particular sample have had pre-menopausal onset, then the observed proportion who are heterozygous for allele a pertains only to the association of a with pre-menopausal breast cancer.

Detecting Genes that Protect Against Disease

The power of the present method is particularly great when compared to that of population tests of associations for disease-protecting effects of specific alleles because, for population tests, the allele frequency must be determined in a very large sample of diseased persons if a significant deviation downward from general population frequency is to be found (18).

Detecting a disease-protecting effect of a specific allele will be of considerable value, because the cellular and biochemical mechanisms through which this protective effect occurs can be studied. When the mechanism of the effect is understood, specific treatments can be based on this understanding to provide preventive therapies for members of the population who do not carry this important disease-protecting allele.

Indifference to Genetic Heterogeneity

It is likely that alleles at several or many different loci predispose to a specific common disease such as breast cancer. Since the statistical power of the present method for testing the association of a single allele with the common disease depends only on the frequency of that particular allele and the strength of the association (as measured by the odds ratio), this power is not affected by the presence of disease-predisposing alleles at other loci. The power of linkage analysis to detect a single locus involved in the etiology of a common disease is, on the other hand, greatly influenced by the degree of underlying genetic heterogeneity (8, 9) unless a single large pedigree is studied.

The present invention is further detailed in the following examples, which are offered by way of illustration only and are not intended to limit the invention in any manner.

Example 1

Ataxia-Telangiectasia

Ataxia-telangiectasia (A-T) is an autosomal recessive syndrome in which the homozygotes have an extraordinarily high cancer risk. Evidence has been published that A-T heterozygotes, who are about one percent of the general population, have an excess risk of cancer, particularly breast cancer (13). Since these findings are of great potential importance to the health of the general population, the pressing scientific issues are to confirm the gene-disease association generally and to establish the specific cancers to which A-T heterozygotes are predisposed.

The method of the present invention is applied in the following way. Detailed clinical information was collected for blood relatives in over 200 families of A-T patients. These patients were the index individuals because they must be homozygous for the A-T allele. Blood or pathology specimens are collected from each relative who has had a cancer, to determine which of these relatives carries the A-T allele by DNA analysis. For each such relative, the A-T allele status is determined with either allele-specific probes or tightly linked polymorphic probes that trace the gene from the index individual to that relative. The A-T gene has been mapped to chromosome 11q22-23 sufficiently closely for this test to be applied. For all cancers and for each hypothesized cancer site, the observed proportion of A-T heterozygotes among the relatives is compared to the null proportion, as described above in the illustrative Example.

EXAMPLE 2

Cystic Fibrosis

Cystic fibrosis (CF) is a well-known autosomal recessive syndrome for which the frequency of heterozygous carriers in the Caucasian population is about five percent. Hypotheses about the CF heterozygote have been proposed: that they are predisposed to chronic lung disease, asthma, allergies, or diabetes mellitus. Evidence from family studies is, at best, unconvincing for each hypothesis. Clinical information about relatives in 30 CF families was collected, and information from an additional 70 CF families is collected. For each of the above hypotheses, blood or pathology specimens are collected for DNA samples to be tested for one or more CF alleles using, for example, the polymerase chain reaction (PCR) (19, 20) for the $delta_{508}$ mutation.

It has been hypothesized that the CF allele frequency is high in Caucasian populations because the CF heterozygote is protected against severe infantile diarrhea. This important hypothesis is tested by collecting DNA from test individuals in CF families, defined by each such individual having had one or more episodes of severe diarrhea. If the hypothesis that the CF allele protects heterozygotes against severe diarrhea is correct, the proportion of CF heterozygotes in this sample of test individuals will be significantly lower than the expected proportion.

Example 3

Alpha$_1$ Antitrypsin

Alpha$_1$ antitrypsin deficiency (PiZZ) causes, in a high proportion of homozygotes, severe progressive emphysema. Despite the several studies that support an excess risk of emphysema for the PiMZ heterozygote, there are enough conflicting data that it is not widely accepted that such heterozygotes, comprising about three percent of the population, are so predisposed (21). A reliable test of this hypothesis has substantial public health implications.

PiZZ homozygotes, identified through population surveys, are the index individuals through whom families are identified. In these families, this hypothesis is tested by comparing, in relatives with emphysema, the observed proportion of PiMZ heterozygotes to the null proportion.

EXAMPLE 4

Breast Cancer

The Michigan Cancer Foundation has collected tissue specimens suitable for DNA analysis from more than 500 patients who had a breast cancer. The association of specific alleles at several different loci is tested in the following way. For example, the "rare" H-ras allele is one allele that is examined.

For each tissue specimen, a living close relative is identified from the comprehensive clinical records. Blood samples for DNA analysis are obtained from each relative. This set of DNA samples is tested to determine which relatives have one of the specific set of H-ras alleles hypothesized to predispose to breast cancer. Then the tissue specimens from the patients whose relative was positive for one of these alleles are tested. As before, the observed proportion is compared to that expected from the null probabilities.

The procedure is repeated with the same set of samples to test any allele system for which the appropriate DNA test is available, such as the retino-blastoma gene (1, 3, 22). This would lead to substantial cost-saving, since the expense of collecting blood samples is amortized over a number of independent tests of hypotheses of allele-breast cancer associations.

EXAMPLE 5

Oncogenes

Oncogenes are genes implicated in the somatic development of tumors; they do not necessarily have a role in inherited predisposition to cancer. Several oncogenes have been studies, and DNA tests exist for them (23–25). There are inherited polymorphisms in many of the oncogenes (29). Small-scale studies have provided some evidence that certain polymorphic alleles of specific oncogenes may predispose to specific cancer types (30–32).

The best example is at the H-ras locus. There is a polymorphism based on a variable number tandem repeat (VNTR) at one end of the gene. The four most common alleles have a frequency of about 95% in the general population; all the remaining alleles are grouped together as the "rare" alleles. Krontiris et al. (16) have found the proportion of these rare alleles in DNA from cancer patients to be higher than that in the control population. It is very important to know for sure whether these constitutive rare H-ras alleles predispose to cancer.

The association between cancer and the rare H-ras alleles is tested in the following way. A volunteer population of, for example, 2,500 unrelated individuals is recruited, and blood samples and family medical histories are obtained from each volunteer. As described above in the general method, there are two alternative routes to arrive at the key sample of test individuals with the disease, breast cancer in the present example. In the first route, each DNA sample from the 2,500 unrelated individuals is tested, and then the family pedigrees for the approximately 250 index individuals with a rare H-ras allele are reviewed. If approximately 40% of the families have a close relative with breast cancer, there will be 100 test individuals with breast cancer in these families to be tested for the rare H-ras allele. In the alternative route of arriving at these 100 individuals with breast cancer in families in which a rare H-ras allele is segregating, the family histories of all 2,500 volunteers is reviewed, the 1,000 in which a relative has had breast cancer are selected, and then the DNA from the volunteers in those 1,000 families is analyzed to determine the 100 index individuals carrying a rare H-ras allele. In either manner, the same 100 breast cancer cases are identified for DNA testing and statistical evaluation. According to the power calculations summarized in the Tables, this sample is fully adequate to test the hypothesized association.

It is instructive to examine how the present process works for a less common cancer such as bladder cancer, and its association with a rare H-ras allele. Bladder cancer is found in a close relative in only 5% of all families. Starting with 2,500 volunteers, only 13 persons with this cancer are found in families in which a rare H-ras allele is segregating. In order to have a sample with adequate statistical power, it would be necessary to start with 7,500 volunteers instead of 2,500. The preferred approach in this instance is to screen first for the 375 families (5% Of 7,500) in which a relative had bladder cancer, and then analyze the volunteer's DNA in each of those families.

EXAMPLE 6

Development of Test Population

The approach described above is applied to any common disease and any allele system that is tested from blood or tissue samples. The apparent limitation is the cost and effort that are required to assemble 1,000 to 20,000 volunteers, collect blood samples from each of them, compile and verify pedigrees for each of them, collect blood samples from the selected diseased relatives, and perform the analytic tests for the allele. Once the database has been prepared, the method of the present invention is performed as described above for any disease-gene association.

Comprehensive testing of hypothesized gene-disease associations is possible with the present invention, because the same panel of volunteers and family medical histories can be used repeatedly to test different gene-disease associations. A panel of 20,000 volunteers is established. Family medical histories and blood samples for serum and DNA analysis are obtained from each volunteer. All instances of common diseases including, but not limited to, cancers, heart disease, hypertension, diabetes mellitus, and psychiatric illnesses, is verified from medical reports. Serum and DNA samples from each relative with one of these diseases are obtained and stored. Then, any hypothesized gene-disease association is tested as described herein. The incremental cost of testing each association will be modest, perhaps $1,000 to 3,000.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

BIBLIOGRAPHY (1) PCT Published Application No. WO89/06703
(2) European Published Application No. 0 259 031
(3) PCT Published Application No. WO87/07472
(4) Cooper, D. N. and Clayton, J. F. (1988). *Hum. Genet.* 78:299–312.
(5) Ebringer, R. W. (1980). *Clinical Science* 59:405–410.
(6) Krontiris, T. G. et al. (1985). *Nature* 313:369–374.
(7) Gerhard, D. S. et al. (1987). *Nature* 325:73–75.
(8) Lander, E. S. et al. (1986). *Proc. Natl. Acad. Sci. USA* 83:7353–7357.
(9) Goldin, L. R. and Gershon, E. S. (1988). *Genetic Epidemiolgy* 5:35–42.
(10) Li, C. C. and Sacks, L. (1954). *Biometrics* 10: 347–360.
(11) Campbell, M. A. and Elston, R. C. (1971). *Ann. Hum. Genet.* 35:225–236.
(12) Woolf, B. (1955). *Ann. Hum. Genet.* 19:251–253.
(13) Swift, M. et al. (1987). *N. Engl. J. Med.* 316: 1289–1294.
(14) Gatti, R. A. et al. (1988). *Nature* 336:577–580.
(15) Breslow, N. E. and Day, N. E. (1987). *IARC Scientific Publications*, No. 82.
(16) Liang, K. Y. (1985). *Biometrika* 72:678–682.
(17) Hall, J. et al. (1988). *Am. J. Hum. Genet.* 43(3), supplement:A24 (Abstract).
(18) Fleiss, J. L. (1981). *Statistical Methods for Rates and Proportions*, end Edition, John Wiley & Sons, New York.
(19) Erlich, H. A., *PCR Technology, Stockton Press, New York* (1989).
(20) Burmer, G. C. et al. (1989). *Cancer Res.* 49:2141–2146.
(21) Hutchison, D. C. S. (1988). Am. J. Med. 84:3–12.
(22) Strong, L. C. et al. (1984). *J. Natl. Cancer Inst.* 73(2):303–311.
(23) U.S. Pat. No. 4,871,838.
(24) PCT Published Application No. WO 87/07472.
(25) U.S. Pat. No. 4,935,341.

(26) Kleinbaum, D. J. et al. (1982). *Epidemiologic Research: Principles and Quantitative Methods*, Lifetime Learning Publications, Belmont, Chapter 8.

(27) Rau, C. R. (1973). *Linear Statistical Inference and Its Applications*, 2nd Ed., Wiley & Sons, New York, Chapter 6.

(28) Rosner, D. (1990). *Fundamentals of Biostatistics*, PWS-Kent, Boston, Chapter 7.

(29) Larsen, C. J. (1988). *Nouv. Rev, Fr. Hematol.* 30 39–43.

(30) Chenevix-Trench, G. et al. (1899). *Intl. J. Cancer* 43:1034–1036.

(31) Opalka, B. et al. (1989). *Blood* 73:814–817.

(32) Kerchuert, J. P. (1990). *Leukemia* 4:16–19.

(33) Swift, M. et al. (1986). *Am. J. Hum. Genet.* 39:573–583.

What is claimed is:

1. A process for selecting a set of families for use in testing an association of an allele and a disease which comprises the steps of:

(a) selecting a population of individuals;

(b) selecting index individuals from said population, said index individuals carrying one or two copies of said allele, the presence of said allele having been determined by analysis of said individuals' macromolecules;

(c) determining the presence of said disease within blood relatives of said index individuals;

(d) selecting test individuals from said blood relatives, said test individuals being persons determined to have said disease; and (e) selecting the set of families, each family having an index individual and at least one test individual.

2. The process of claim 1 wherein said population comprises between 2,500 and 20,000 individuals.

3. The process of claim 1 wherein said population comprises between 5,000 and 20,000 individuals.

4. The process of claim 1 wherein said population comprises between 10,000 and 20,000 individuals.

5. The process of claim 1 wherein said population comprises between 15,000 and 20,000 individuals.

6. A process for determining the association of an allele and a disease which comprises the steps of:

(a) selecting a disease and an allele;

(b) identifying a set of index individuals who are homozygous or heterozygous for said allele, the presence of said allele having been determined by analysis of said individuals' macromolecules;

(c) selecting a set of families, each family comprising an index individual and blood relatives of said index individual, wherein at least one blood relative has said disease;

(d) selecting test individuals for each index individual, said test individual is a blood relative having said disease;

(e) determining a first proportion which is the proportion of test individuals who carry said allele, the presence of said allele having been determined by analysis of said test individuals' macromolecules;

(f) determining a second proportion which is the proportion of test individuals expected to carry said allele if there is no association between said allele and said disease; and (g) comparing the first and second proportions, whereby a statistically significant difference indicates that said allele is associated with said disease.

7. The process of claim 6 wherein said second proportion is the null probability.

8. The process of claim 6 wherein said comparison of said first and second proportions is performed using the score statistic.

9. The process of claim 6 wherein the strength of the association is calculated by the odds ratio.

10. A process according to claim 6 wherein one test individual is selected from a family if said index individual is heterozygous for said allele.

11. A process according to claim 6 wherein if said index individual is homozygous for said allele one test individual is selected from either a maternal or from a paternal lineage.

12. A process according to claim 6 wherein if said index individual is homozygous for said allele two test individuals are selected, one of said test individuals being selected from a maternal lineage and the other of said test individuals being selected from a paternal lineage.

13. A process for selecting a set of families for use in testing an association of an allele and a disease which comprises the steps of:

(a) selecting a population of individuals with said disease;

(b) testing one blood relative of each individual from said population to determine which relative carries one or two copies of said allele, the presence of said allele being determined by analysis of each blood relative's macromolecules;

(c) designating the blood relatives who carry said allele as the index individuals and the specific members of the said population who are related to each index individual as the test individuals; and (d) selecting the set of families, each family having an index individual and a test individual who is a relative having said disease.

14. The process of claim 13 wherein said population comprises between 2,500 and 20,000 individuals.

15. The process of claim 13 wherein said population comprises between 5,000 and 20,000 individuals.

16. The process of claim 13 wherein said population comprises between 10,000 and 20,000 individuals.

17. The process of claim 13 wherein said population comprises between 15,000 and 20,000 individuals.

* * * * *